United States Patent [19]

Köhn et al.

[11] Patent Number: 4,758,337
[45] Date of Patent: Jul. 19, 1988

[54] FILTER FOR FILTERING HUMAN BLOOD, ESPECIALLY IN AN EXTRACORPOREAL CIRCULATORY SYSTEM

[75] Inventors: Heinz-Gerhard Köhn, Dransfeld; Günter Pradel, Göttingen, both of Fed. Rep. of Germany

[73] Assignee: Sartorius GmbH, Fed. Rep. of Germany

[21] Appl. No.: 928,059

[22] Filed: Nov. 7, 1986

[30] Foreign Application Priority Data

Nov. 23, 1985 [DE] Fed. Rep. of Germany ....... 3541521

[51] Int. Cl.⁴ .................. B01D 19/00; B01D 35/30
[52] U.S. Cl. .................................. 210/94; 55/178; 210/103; 210/188; 210/436; 210/438; 210/472; 210/493.1; 210/149
[58] Field of Search ............... 55/178; 210/188, 436, 210/438, 472, 493.1, 497.01, 94, 103, 149; 604/4

[56] References Cited

U.S. PATENT DOCUMENTS 3,701,433 10/1972 Krakauer ........................ 210/436
3,993,461 11/1976 Leonard et al. ................. 55/178

FOREIGN PATENT DOCUMENTS 275316 7/1970 U.S.S.R. ............................. 604/4

Primary Examiner—Peter Hruskoci
Assistant Examiner—W. Gary Jones
Attorney, Agent, or Firm—Eric P. Schellin

[57] ABSTRACT

In a filter for filtering human blood, especially in an extracorporeal circulatory system, with a blood inlet, a blood outlet and a vertically directed, hollow, cylindrical filter element located between them and consisting of a filter, and in which the hollow, cylindrical filter element seals housing chambers located in the filter housing between the blood inlet and the blood outlet in such a manner from each other by means of its front surfaces that the blood can only flow through the filter element, whereby the blood inlet is located in the center of the housing and of the hollow, cylindrical filter element and a gas outlet is located at the highest point of the housing, the blood inlet runs axially through the hollow cylinder of the filter element as a central ascending tube and divides it cross section into a smaller ascending pipe section and into a settling chamber section for the blood which is several times larger. The settling chamber section empties in its extended axis into a cylindrical gas separation chamber which comprises a closable gas outlet. The blood outlet is provided in the area of the lowest active filter surface of the filter element as a horizontally projecting connection piece which communicates only with an annular space surrounding the outside of the filter element. The annular space is located in the area of the upper active filter surface of the filter element and comprises its own closable gas outlet at the highest point of an annular space, which runs preferably obliquely to the vertical filter axis.

9 Claims, 2 Drawing Sheets

FILTER FOR FILTERING HUMAN BLOOD, ESPECIALLY IN AN EXTRACORPOREAL CIRCULATORY SYSTEM

BACKGROUND OF THE INVENTION

The invention relates to a filter for filtering human blood, especially in an extracorporeal circulatory system. In a known blood filter of this type (DE-PS No. 21 55 820) the filter is designed in an essentially dynamically balanced manner, whereby blood inlet and blood outlet are located in the axis of rotation of the housing. A gas outlet valve is provided at the highest point of the blood outlet chamber, that is, on the arterial side of the filter element. The filter element itself is designed as a hollow, cylindrical filter member whose front surfaces are each enclosed by an end cap in a sealing manner, whereby the upper end cap closes the hollow cylindrical space in the extension of the blood inlet so that the blood flows from the inner cylinder space through the filter member into the outer cylinder space.

The filter element has the task of filtering microemboli out of the blood and the gas outlet valve on the patient side of the filter element has the task of discharging gas bubbles which collect at the highest point of the cylinder housing to the outside in order to avoid gas emboli.

Such filters are operated in a vertical position in conjunction with a heart-lung machine, whereby it is located in a customary arrangement of the filter over the heart-lung machine and the outlet of the blood filter on the patient side is located approximately at the level of the patient.

The known filter according to the generic part of the main claim is in need of improvement in as far as the blood outlet of the filter on the patient side is vertically directed and bends of the connection hose located on the filter outlet and running laterally to the patient frequently occur.

Filters are also known in which both connections project axially downward so that similar problems occur here too and the connections conceal an additional safety risk. Another safety risk in the known filters is the fact that the blood transported out of the heart-lung machine does not have sufficient opportunity to become quiescent within the filter housing so that this increases the danger of gas emboli.

Such filter are frequently employed in open heart operations and on other organs, as is described in DE-PS No. 32 04 317 and in the article "Myocardial 'Equilibration Processes' and Myocardial Energy Turnover during Initiation of Articicifial Cardiac Arrest with Cardioplegic Solution-Reasons for a Sufficiently Long Cardioplegic Perfusion" published in "Thorac. Cardiovasc. Surgeon" 29, 1981, pp. 71–6. In such operations the blood or a cardioplegic solution is cooled down to approximately $+4°$ to $+6°$ C. in the heart-lung machine. The design of the known filters does not offer any possibility of detecting by measuring techniques the development of air bubles in the fluid to be filtered and the temperature of the liquid in the filter. This is only possible in the individual line sections outside of the filter.

The known filters (EP-OS No. 82 721 = U.S. Ser. No. 333,832, U.S. Pat. No. 3,701,433) are usually constructed of transparent plastic in four and more parts. In spite of the transparency, on account of the housing construction and the arrangement of the filter element within this construction, only either the one or the other chamber side of the housing can be observed for the formation of gas bubbles and vented. In order to remove the enclosed gas during the filling of the filter, it is made possible for the enclosed gas in the non-ventable chamber to escape into the ventable chamber by rotating the filter by 180°. This procedure must usually be performed several times, is unsatisfactory as concerns manipulation and is not without risk from a medical point of view.

The invention therefore has the task of improving with simple means a filter as concerns its manipulation during venting and its operational safety as regards the dangers inherent in the formation of gas bubbles and in the bending of the connection hose to the patient without increasing the number of its individual parts, which would increase the expense.

BRIEF DESCRIPTION OF THE INVENTION

The filter, which is formed by only three individual elements, namely, two housing parts and the filter element integrated therein, comprises a blood inlet which is located directly over the heart-lung machine, continues into a central ascending pipe, extends through practically the entire length of the hollow cylinder of the filter element and ends in a gas separation chamber which is preferably cylindrical, continues upward and has sufficient volume to bring gas bubbles in the blood or in the liquid to be filtered to separation. The central ascending pipe is enclosed by a settling chamber with a larger cross section in which the blood has the opportunity to become quiescent before it passes radially through the filter medium cloth of the pleated filter element to the outside on the arterial side or patient side of the filter. The bending of connection hoses can be avoided by the horizontally projecting blood outlet because it is optimally positioned both in relation to the heart-lung machine and to the position of the patient.

DETAILED DESCRIPTION OF THE INVENTION

The concept of the invention is explained in more detail in a preferred embodiment.

Figure 1:
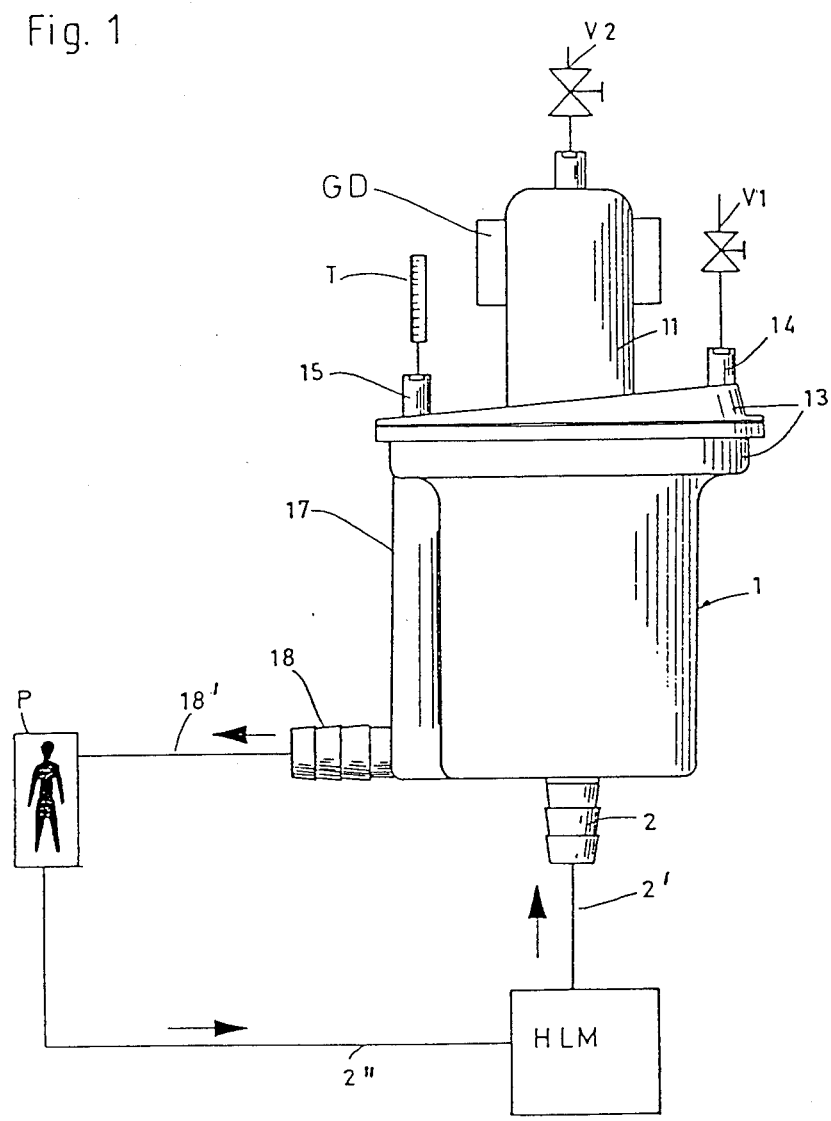
FIG. 1 shows the filter in a side view, supplemented by schematically indicated insert means for the insertion of the filter in the cited operating techniques.
Figure 2:
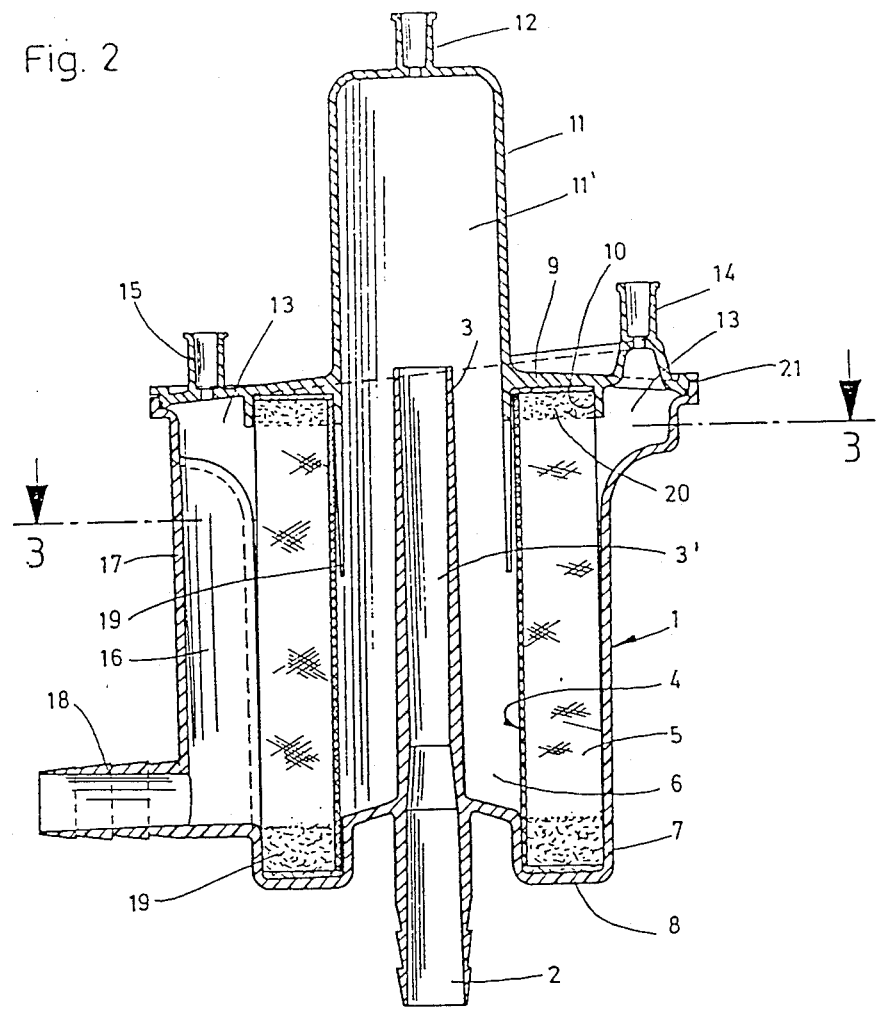
FIG. 2 shows a vertical section through the filter along line 2—2 in FIG. 3.
Figure 3:
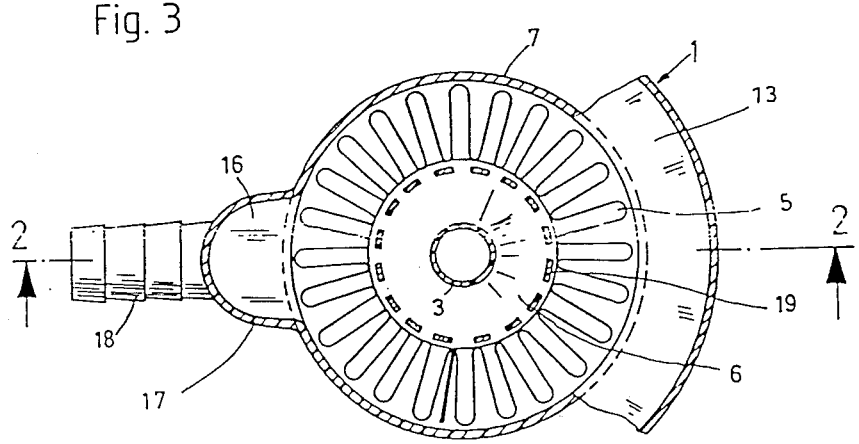
FIG. 3 shows a horizontal section through the filter along line 3—3 in FIG. 2.

The filter according to FIG. 1 consists essentially of the two housing parts 7, 9 and hollow cylindrical filter element 5 integrated therein. The two housing parts 7, 9 are permanently connected by means of an interlocking housing profiling at 21 by adhesion or ultrasound welding.

Housing part 7 comprises central lower blood inlet 2, which is extended axially in the form of ascending pipe 3 and extends through substantially the entire hollow cylinder 4 of filter element 5. Hollow cylinder 4 is divided by ascending pipe 3 into settling chamber 6, which is two to five times greater in section. Housing part 7 also comprises U-shaped receiving bearing 8 in the lower area for receiving the lower front surface of filter element 5 and for receiving sealing means 19, with which the sealing connection between the lower end of filter element 5 and receiving bearing 8 is achieved. The active filter surface of filter element 5 begins above receiving bearing 8. Blood outlet 18 is provided in this area as radial connection piece 18. Blood outlet 18 is connected via collection shaft 16 in the form of radially projecting housing convexity 17 to annular space 13 formed in housing part 7 in it supper area.

The other housing part 9 forms the extension of obliquely rising collection chamber 13 on its circumference and carries connection 14 for receiving a venting valve on its highest point of collection chamber 13. Another connection piece 15 is provided diametrically opposite in housing part 9, which piece is located in the axial extension of collection shaft 16 . This connection piece 15 and the collection shaft 16 form a receiving bearing for temperature sensor T or a thermometer, as is indicated in FIG. 1. Housing part 9 also comprises a U-shaped receiving bearing 10 for receiving the upper end of filter element 5 and of sealing means 20.

Above ascending pipe 3 and settling chamber 6, the latter is extended by cylindrical housing section 11, which forms gas separation chamber 11' and also ends in a connection piece 12. As is schematically indicated in FIG. 1, connection pieces 12, 14, which are designed as luer locks, are equipped with two-way valves V2, V1.

Housing section 11 for gas separation chamber 11' is cylindrical and dimensioned so that the outside can be surrounded by gas bubble detectors GD customary in trade (as indicated in FIG. 1). Such gas bubble detectors usually operate on the basis of ultrasound and release an alarm at an increased occurrence of gas bubbles.

Finger-shaped mounting aids 19 are integrated into component 9 and have the task of simplifying a centering of hollow cylindrical filter element 5.

Filter element 5 consists of a fabric, preferably polyester monofilaments with a thread thickness of 30 m and a mesh width (inside distance of the threads) of 40 m or the mesh width is between 20 m and 40 m. The fabric is preferably a twill weave. The fabric can also be supplemented with another filter layer in the form of a filter fleece of plastic monofilaments which is positioned upstream in front of the actual filter fabric.

The filter housing consists preferably of transparent plastic, e.g. polyester. The sealing means consists of polyurethane, which has already proven to be very satisfactory in the field of medicine. The ends of the filter fabric, optionally with filter fleece, are welded to each other.

FIG. 1 makes clear the logical shaping of filter 1. P indicates the patient, from whom hose line 2'' runs directly as venous line into a heart-lung machine. Line 2' runs directly from heart-lung machine HLM into blood inlet connection piece 2 located at the bottom. The filtered blood leaves filter 1 through filter element 5, collection shaft 17 and blood outlet 18, which runs out horizontally via (arterial) hose line 18' to patient P. A bending of the hose lines is prevented by the logical arrangement of connections 2, 18.

Both the unclean side 2, 3, 11', 4 and the clean side 13, 16, 18 of filter 1 has its own gas outlet or gas collection chamber located at the highest point and both sides can be inspected visually so that safety is considerably increased and the manipulation of filter 1 is improved without a greater number of individual parts having to be purchased to this end.

We claim:

1. A filter for filtering human blood in an extracorporeal circulatory system, comprising a housing having a blood inlet and a blood outlet, two housing parts permanently connected defining housing chambers and containing a receiving bearing which contains a temperature sensor for filtered blood a vertically directed hollow cylindrical filter element integrated therein, said filter element is located between the blood inlet and the blood outlet and seals, the housing chambers between the blood inlet and the blood outlet to allow blood to flow only through the filter element, whereby the blood inlet is axially located in the center of the housing as a central ascending pipe (3) and the hollow cylindrical filter element, and a gas outlet 12 is located at the highest point of the housing; the hollow cylinder (4) of the filter element (5) empties in its axis of extension into a cylindrical gas separation chamber (11') which comprises the gas outlet (12) said gas outlet being closable and the blood outlet (18) is in the area of the lower end of the filter element (5) as an extending connection piece which communicates with the annular space (13) and with a second gas outlet (14) which annular space encloses the outer side of the filter element (5), wherein said gas separation chamber (11') is formed by an axial housing extension (11) and the latter is cylndrically formed in order to receive an enclosing gas bubble detector; said housing comprises on an inner side of its upper and lower front surface of a formed receiving bearing (10) with a U-shaped cross section for front surfaces of the hollow cylindrical filter elements and sealing means (20) which connect the front surfaces to the housing.

2. The filter according to claim 1, wherein the annular space (13) is located in the area of the upper filter surface of the filter element (5), the second gas outlet (14) is closable and is located at the highest point of the annular space (13), which runs obliquely to the vertical filter axis.

3. The filter according to claim 1, wherein the blood outlet (18) is constructed as a horizontally extending connection piece and communicates with the annular space (13) via a vertical collection shaft (16).

4. The filter according to claim 3, wherein the vertical collection shaft (16) is formed by a radial housing convexity which is open to the filter element (5).

5. The filter according to claim 4, wherein the collection shaft (16) terminates axially in a closable opening (15) in one of the housing parts and said closable opening (15) and said collection shaft (16) form said receiving bearing for the temperature sensor (T) disposed therein.

6. The filter according to claim 5, wherein closable opening (15) with connection shaft (16) is located diametrically opposite said second gas outlet (14) of the annular space (13).

7. The filter according to claim 1, wherein the filter element (5) is formed by a single-layer or multi-layer cloth consisting of woven and non-woven plastic monofilaments folded in a plurality of folds.

8. The filter according to claim 1, wherein the housing (7,9) is formed from transparent plastic and the two housing parts (7,9) directly receive the hollow cylindrical filter element (5) and are permanently connected at their edges in a leakproof manner by an interlocking profiling.

9. The filter according to claim 1, wherein the ascending pipe (3) axially penetrates the hollow cylinder (4) of the filter element (5).

* * * * *